US009528976B2

(12) United States Patent
Pani et al.

(10) Patent No.: US 9,528,976 B2
(45) Date of Patent: Dec. 27, 2016

(54) METHOD FOR DETECTION OF ADENOSINE AND METABOLITES THEREOF

(71) Applicant: St. Jude Children's Research Hospital, Memphis, TN (US)

(72) Inventors: Amar K. Pani, Lakeland, TN (US); Richard Jay Smeyne, Collierville, TN (US)

(73) Assignee: St. Jude Children's Research Hospital, Memphis, TN (US)

( * ) Notice: Subject to any disclaimer, the term of this patent is extended or adjusted under 35 U.S.C. 154(b) by 0 days.

(21) Appl. No.: 14/765,649

(22) PCT Filed: Feb. 28, 2014

(86) PCT No.: PCT/US2014/019215
§ 371 (c)(1),
(2) Date: Aug. 4, 2015

(87) PCT Pub. No.: WO2014/134379
PCT Pub. Date: Sep. 4, 2014

(65) Prior Publication Data
US 2016/0003797 A1 Jan. 7, 2016

Related U.S. Application Data

(60) Provisional application No. 61/770,418, filed on Feb. 28, 2013.

(51) Int. Cl.
| | |
|---|---|
| *G01N 27/42* | (2006.01) |
| *G01N 33/487* | (2006.01) |
| *A61K 31/52* | (2006.01) |
| *B01D 15/32* | (2006.01) |
| *G01N 30/34* | (2006.01) |
| *G01N 30/64* | (2006.01) |
| *G01N 30/88* | (2006.01) |

(52) U.S. Cl.
CPC ......... *G01N 33/48707* (2013.01); *A61K 31/52* (2013.01); *B01D 15/327* (2013.01); *G01N 27/423* (2013.01); *G01N 30/34* (2013.01); *G01N 30/64* (2013.01); *G01N 2030/8827* (2013.01); *Y10T 436/141111* (2015.01); *Y10T 436/142222* (2015.01); *Y10T 436/147777* (2015.01); *Y10T 436/173845* (2015.01); *Y10T 436/25375* (2015.01)

(58) Field of Classification Search
CPC ..... A61K 31/52; B01D 15/325; B01D 15/327; G01N 2030/8827; G01N 27/423; G01N 30/02; G01N 30/34; G01N 30/64; G01N 33/48; G01N 33/48707; Y10T 436/14; Y10T 436/141111; Y10T 436/142222; Y10T 436/143333; Y10T 436/145555; Y10T 436/147777; Y10T 436/17; Y10T 436/173845; Y10T 436/20; Y10T 436/203332; Y10T 436/25; Y10T 436/25375
USPC ..... 436/63, 91, 92, 93, 94, 96, 98, 106, 111, 436/127, 131, 161, 149, 174, 177; 422/70, 422/82.01
See application file for complete search history.

(56) References Cited

U.S. PATENT DOCUMENTS 6,395,256 B1   5/2002  Osswald et al. ............. 424/1.69

FOREIGN PATENT DOCUMENTS

WO   WO99/34210   12/1998

OTHER PUBLICATIONS

Pappa-Louisi et al. Journal of Liquid Chromatography and Related Technology, vol. 23 (4), 2000, pp. 505-521.*
Deng et al. Analyst, vol. 128, 2003, pp. 1013-1018.*
Allgaier et al. "Studies on the Interaction Between Presynaptic α2-Adrenoceptors and Adenosine $A_1$ Receptors Located on Noradrenergic Nerve Terminals" Naunyn Schmiedebergs Arch. Pharmacol. 1991 344:187-92.
Berman et al. "Evidence for Increased Dorsal Hippocampal Adenosine Release and Metabolism during Pharmacologically Induced Seizures in Rats" Brain Res. 2000 872:44-53.
Betto et al. "Simultaneous High-Performance Liquid Chromatographic Determination of Adenosine and Dopamine in Rat Striatal Tissue with Combined Ultraviolet Absorbance and Electrochemical Detection" Journal of Chromatography B 1992 662:21-25.
Birbeck, J.A. & Mathews, T.A. "Simultaneous Detection of Monoamine and Purine Molecules Using High-Performance Liquid Chromatography with a Boron-Doped Diamond Electrode" Anal. Chem. 2013 85:7898-404.
Boison, D. "Adenosine Dysfunction in Epilepsy" Glia 2012 60:1234-43.
Boison et al. "Adenosine Hypothesis of Schizophrenia—Opportunities for Pharmacotherapy" Neuropharmacology 2012 62:1527-43.
Burdett et al. "Efficient Determination of Purine Metabolites in Brain Tissue and Serum in High-Performance Liquid Chromatography with Electrochemical and UV Detection" Biomed. Chromatograph. 2012 27:122-129.
Burgos et al. "Luciferase-Based Assay for Adenosine: Application to S-Adenosyl-L-homocysteine Hydrolase" Anal. Chem. 2012 84:3593-8.
During, M.J. & Spencer, D.D. "Adenosine: A Potential Mediator of Seizure Arrest and Postictal Refractoriness" Ann. Neurol. 1992 32:618-24.
Ferre et al. "Adenosine $A_{2A}$ Receptors in Ventral Striatum, Hypothalamus and Nociceptive Circuitry Implications for Drug Addiction, Sleep and Pain" Prog. Neurobiol. 2007 83:332-47.

*Primary Examiner* — Maureen Wallenhorst
(74) *Attorney, Agent, or Firm* — Licata & Tyrrell P.C.

(57) ABSTRACT

This invention relates is a label-free, enzyme-free, aptamer-free method for simultaneously measuring adenosine, and its intracellular metabolites, e.g., AMP, ADP and ATP, using high pressure liquid chromatography coupled to electrochemical detector (HPLC-ECD).

7 Claims, No Drawings

(56) References Cited

OTHER PUBLICATIONS

Ferre et al. "Stimulation of High-Affinity Adenosine $A_2$ Receptors Decreases the Affinity of Dopamine $D_2$ Receptors in Rat Striatal Membranes" Proc. Natl. Acad. Sci. USA 1991 88:7238-41.
Fredholm et al. "Adenosine and Brain Function" Int. Rev. Neurobiol. 2005 63:191-270.
Fredholm et al. "Actions of Caffeine in the Brain with Special Reference to Factors that Contribute to its Widespread Use" Pharmacol. Rev. 1999 51:83-133.
Gomes et al. "Adenosine Receptors and Brain Diseases: Neuroprotection and Neurodegeneration" Biochim. Biophys. Acta 2011 1808:1380-99.
Henderson, R.J. & Griffin, C.A. "Electrochemical Detection of Adenosine and Other Purine Metabolites during High-Performance Liquid Chromatographic Analysis" J. Chromatograph. A 1984 298:231-42.
Hohoff et al. "Adenosine $A_{2A}$ Receptor Gene: Evidence for Association of Risk Variants with Panic Disorder and Anxious Personality" J. Psychiatr. Res. 2010 44:930-7.
Huang, P.J, & Liu, J. "Flow Cytometry-Assisted Detection of Adenosine in Serum with an Immobilized Aptamer Sensor" Anal. Chem. 2010 82:4020-26.
Huang et al. "Time-resolved Fluorescence Biosensor for Adenosine Detection based on Home-made Europium Complexes" Biosens. Bioelectron. 2011 29:178-83.
Jackisch et al. "Endogenous Adenosine as a Modulator of Hippocampal Acetylcholine Release" Naunyn Schmiedebergs Arch. Pharmacol. 1984 327:319-25.
Jin, S. & Fredholm, B.B. "Adenosine $A_2$ Receptor Stimulation Increases Release of Acetylcholine from Rat Hippocampus but not Striatum, and Does Not Affect Catecholamine Release" Naunyn Schmiedebergs Arch. Pharmacol. 1997 355:48-56.
Khlyntseva et al. "Methods for the Determination of Adenosine Triphosphate and Other Adenine Nucleotides" Journal of Analytical Chemistry 64(7):657-673 2009.
Kim et al. "Label-free Electrochemical Detection of Adenosine based on Electron Transfer from Guanine Bases in an Adenosine-Sensitive Aptamer" Chem. Commun. 2009 31:4747-9.
Kirk I.P. & Richardson, P.J. "Inhibition of Striatal GABA Release by the Adenosine $A_{2a}$ Receptor is Not Mediated by Increases in Cyclic AMP" J. Neurochem. 1995 64:2801-9.
Lazarus et al. "Arousal Effect of Caffeine Depends on Adenosine $A_{2A}$ Receptors in the Shell of the Nucleus Accumbens" J. Neurosci. 2011 31:10067-75.
Li et al. "Detection of Adenosine Triphosphate with an Aptamer Biosensor Based on Surface-Enhanced Raman Scattering" Anal. Chem. 2012 84:2837-2842.
Liu, J-M. & Yan, X-P. "Competitive Aptamer Bioassay for Selective Detection of Adenosine Triphosphate Based on Metal-Paired Molecular Conformational Switch and Fluorescent Gold Nanoclusters" Biosens. Bioelectron. 2012 36:135-41.
Pani et al. "Neurochemical Measurement of Adenosine in Discrete Brain Regions of Five Strains of Inbred Mice" PLOS One 2014 9(3):e92422.
Pedata et al. "Effect of Adenosine, Adenosine Triphosphate, Adenosine Deaminase, Dipyridamole and Aminophylline on Acetylcholine Release from Electrically-Stimulated Brain Slices" Neuropharmacol. 1983 22:609-614.
Phillis, J.W. & Wu, P.H. "The Role of Adenosine and its Nucleotides in Central Synaptic Transmission" Prog. Neurobiol. 1981 16:187-239.
Porkka-Heiskanen, T. & Kalinchuk, A.V. "Adenosine, Energy Metabolism and Sleep Homeostasis" Sleep Med. Rev. 2011 15:123-35.
Rodrigues et al. "Co-localization and Functional Interaction between Adenosine $A_{2A}$ and Metabotrobic Group 5 Receptors in Glutamatergic Nerve Terminals of the Rat Striatum" J. Neurochem. 2005 92:433-41.
Schwarzschild et al. "Targeting Adenosine $A_{2A}$ Receptors in Parkinson's Disease" Trends Neurosci. 2006 29:647-54.
Sebastiao, A.M. & Ribeiro, J.A. "Adenosine Receptors and the Central Nervous System" Handb. Exp. Pharmacol. 2009 471-534.
Shibue et al. "The Perchlorate Anion is More Effective than the Trifluoracetate Anion as an Ion-Pairing Reagent for Reversed-phase Chromatography of Peptides" J. Chromatogr. A 2005 1080(1):49-57.
Simpson et al. "A Highly Sensitive Assay for Adenosine Triphosphate Employing an Improved Firefly Luciferase Reagent" Lett. Appl. Microbiol. 2008 11:208-10.
Snyder, S.H. "Adenosine as a Neuromodulator" Annu. Rev. Neurosci. 1985 8:103-124.
Wardas, J. "Neuroprotective Role of Adenosine in the CNS" Pol. J. Pharmacol. 2002 54:313-26.
Wei et al. "Selective Inactivation of Adenosine $A_{2A}$ Receptors in Striatal Neurons Enhances Working Memory and Reversal Learning" Learn. Mem. 2011 18:459-74.
Yan et al. "Label-free Aptamer-based Chemiluminescence Detection of Adenosine" Talanta 2009 79:383-87.
Zetterström et al. "Purine Levels in the Intact Rat Brain, Studies with an Implanted Perfused Hollow Fibre" Neurosci. Lett. 1982 29:111-115.
Zhou et al. "A New Strategy for the Detection of Adenosine Triphosphate by Aptamer/Quantum Dot Biosensor based on Chemiluminescence Resonance Energy Transfer" Analyst 2012 137:4262-6.
International Search Report and Written Opinion in PCT/US14/19215, Jun. 2, 2014.
International Preliminary Report on Patentability in PCT/US14/19215, Sep. 1, 2015.

* cited by examiner

METHOD FOR DETECTION OF ADENOSINE AND METABOLITES THEREOF

This application is a U.S. National Stage Application of PCT/US2014/019215 filed Feb. 28, 2014 and claims the benefit of priority from U.S. patent application Ser. No. 61/770,418, filed Feb. 28, 2013, the contents of each of which are incorporated herein by reference in their entirety.

BACKGROUND

Purine and pyrimidine nucleosides and bases, the essential building blocks of nucleic acids, occur widely throughout the animal kingdom and underlie a number of critical functions including energy transduction, metabolism and cell signaling. One endogenous purine nucleoside, adenosine (ADO), plays an important role in a number of biochemical processes including energy transfer.

In the nervous system, ADO acts as a non-classical inhibitory neurotransmitter (Pedata, et al. (1983) *Neuropharmacol.* 22:609-614; Jackisch, et al. (1984) *Naunyn Schmiedebergs Arch. Pharmacol.* 327:319-25) and neuromodulator (Phillis & Wu (1981) *Prog. Neurobiol.* 16:187-239; Snyder (1985) *Annu. Rev. Neurosci.* 8:103-124). Alterations in adenosine or its signaling have been linked to a number of neurological disorders including epilepsy (Boison (2012) *Glia* 60:1234-43), Parkinson's disease (Wardas (2002) *Pol. J. Pharmacol.* 54:313-26; Schwarzschild, et al. (2006) *Trends Neurosci.* 29:647-54), schizophrenia (Boison, et al. (2012) *Neuropharmacology* 62:1527-43), panic disorder and anxiety (Hohoff, et al. (2010) *J. Psychiatr. Res.* 44:930-7), as well as drug abuse (Ferre, et al. (2007) *Prog. Neurobiol.* 83:332-47). Alterations in ADO have also been linked to changes in a sleep and arousal (Porkka-Heiskanen & Kalinchuk (2011) *Sleep Med. Rev.* 15:123-35) as well as cognition and memory (Wei, et al. (2011) *Learn. Mem.* 18:459-74; Fredholm, et al. (2005) *Int. Rev. Neurobiol.* 63:191-270).

With the brain, extracellular ADO concentrations have been reported to be in the 30-400 nM range (Fredholm, et al. (1999) *Pharmacol. Rev.* 51:83-133; Zetterström, et al. (1982) *Neurosci. Lett.* 29:111-115). However, in response to cellular damage (e.g., seizure or ischemia), these concentrations can quickly elevate (Zetterström, et al. (1982) supra; Berman, et al. (2000) *Brain Res.* 872:44-53), in some cases 7.5-31-fold (During & Spencer (1992) *Ann. Neurol.* 32:618-24), suggesting that ADO, in addition to signaling, also can have a neuroprotective function.

Adenosine functions by binding to and signaling through four known receptor subtypes (A1, A2A, A2B, and A3) (Gomes, et al. (2011) *Biochim. Biophys. Acta* 1808:1380-99; Sebastiao & Ribeiro (2009) *Handb. Exp. Pharmacol.* 471-534). One of the best-known compounds that acts via ADO signaling, and in particular by bind to the A2A receptor, is caffeine. This drug's stimulatory effects are primarily (although not entirely) credited to its inhibition of ADO via competitive inhibition of these receptors (Lazarus, et al. (2011) *J. Neurosci.* 31:10067-75), effectively blocking adenosine signaling. The subsequent reduction in ADO signaling leads to increased activity of other neurotransmitters including acetylcholine (Jin & Fredholm (1997) *Naunyn Schmiedebergs Arch. Pharmacol.* 355:48-56), noradrenaline (Allgaier, et al. (1991) *Naunyn Schmiedebergs Arch. Pharmacol.* 344:187-92), GABA (Kirk & Richardson (1995) *J. Neurochem.* 64:2801-9), dopamine (Ferre, et al. (1991) *Proc. Natl. Acad. Sci. USA* 88:7238-41) and glutamate (Rodrigues, et al. (2005) *J. Neurochem.* 92:433-41).

Conventionally, the ability to directly measure adenosine and its metabolites has been difficult, and has generally been carried out by proxy. For example, aptamer-based approaches have been described (Zhou & Zhao (2012) *Analyst* 137:4262-6; Liu & Yan (2012) *Biosens. Bioelectron.* 36:135-41; Li, et al. (2012) *Anal. Chem.* 84:2837-2842; Huang & Liu (2010) *Anal. Chem.* 82:4020-26; Yan, et al. (2009) *Talanta* 79:383-87; Kim, et al. (2009) *Chem. Commun.* 31:4747-9), as have label-based (Huang, et al. (2011) *Biosens. Bioelectron.* 29:178-83) and enzyme-based, e.g., luciferase (Burgos, et al. (2012) *Anal. Chem.* 84:3593-8; Simpson, et al. (2008) *Lett. Appl. Microbiol.* 11:208-10)or S-adenosylhomocysteine hydrolase (WO 1999/034210; U.S. Pat. No. 6,395,256) approaches.

More direct approaches have also been suggested. For example, a combined high pressure liquid chromatography (HPLC) separation and electrochemical detection method has been described for identifying adenosine and guanosine (Henderson & Griffin (1984) *J. Chromatgraph. A* 298:231-42). However, clean-up procedures were suggested to remove interfering material in biological samples. Similarly, a combined reversed-phase HPLC, gradient elution and electrochemical and UV detection method has been described for detecting adenosine, guanosine, inosine, guanine, hypoxanthine, xanthine and urate in mouse brain and serum, as well as in post-mortem human brain (Burdett, et al. (2012) *Biomed. Chromatograph.* Doi:10.1002/bmc.2760). Moreover, simultaneous detection of dopamine and adenosine has been described using a boron-doped diamond working electrode in combination with HPLC (Birbeck & Mathews (2012) *Pittcon* 2012, Abstract 1370-3; Birbeck & Mathews (2013) *Anal. Chem.* 85:7898-404).

SUMMARY OF THE INVENTION

The present invention is a method for simultaneously detecting adenosine, and its metabolites, by (i) separating the components of a biological sample by reversed phase high pressure liquid chromatography under isocratic elution conditions; (ii) collecting fractions; and (iii) simultaneously detecting the levels of adenosine, and metabolites thereof, in each fraction with a coulometric electrochemical detector. In one embodiment, the method also includes the step of comparing the detected levels of adenosine, and metabolites thereof, with a standard curve to quantitate the amount of adenosine, and metabolites thereof, present in the biological sample. In other embodiment, step (i) is carried out under acidic conditions or with a mobile phase containing sodium perchlorate and acetonitrile at a pH in the range of 2 to 4. In a further embodiment, the adenosine metabolites include adenosine monophosphate, adenosine diphosphate, and adenosine triphosphate.

DETAILED DESCRIPTION OF THE INVENTION

Alterations in the levels of adenosine have been correlated with a number of neurological diseases including Parkinson's disease, Schizophrenia, Epilepsy, Stroke, Panic Disorder and other Psychiatric diseases as well as immunological syndromes. Measurement of adenosine monophosphate (AMP), adenosine diphosphate (ADP), adenosine triphosphate (ATP) and adenosine (ADO) can be used to examine cellular bioenergetics. Therefore, a rapid means for detecting adenosine and its metabolites provides a means for diagnosing such diseases as well as for monitoring therapeutic treatment of the same.

A label-free, enzyme-free, aptamer-free method for simultaneously measuring the purine neurotransmitter adenosine, and its intracellular metabolites, e.g., AMP, ADP and ATP, using high pressure liquid chromatography coupled to electrochemical detector (HPLC-ECD) has now been developed. Using this method, adenosine and its nucleoside metabolites were measured from several brain regions, including brainstem, cerebellum, cortex, hippocampus, olfactory bulb, substantia nigra and striatum, in a number of common inbred mouse strains (C57BL/6, Swiss-Webster, FVB/J, 129P/J, and BALB/c) that are typically used to develop neurodegenerative disease models. It was found that levels of adenosine and the nucleoside metabolites vary significantly among the different regions and mouse strains examined. In regard to adenosine, C57BL/6 mice had the lowest levels in brain while BALB/c mice have the highest. It is possible that differences in baseline adenosine levels contribute to differential strain effects seen in the expressed phenotypes of neurodegenerative mouse models.

According to one embodiment of the invention, the method comprises the steps of: separating the components of a biological sample by reversed phase HPLC under isocratic elution conditions, collecting fractions, and simultaneously detecting the levels of adenosine, and intracellular metabolites thereof, in each fraction with a coulometric electrochemical detector. In some embodiments, that method also includes comparing the detected levels with a standard curve to determine the amount of total adenosine, and intracellular metabolites thereof, present in the original sample. In another embodiment, the method consists of the steps of: separating the components of a biological sample by reversed phase HPLC under isocratic elution conditions; collecting fractions; simultaneously detecting the levels of adenosine, and intracellular metabolites thereof in each fraction with an coulometric electrochemical detector; and comparing the detected levels with a standard curve to determine the amount of total adenosine, and intracellular metabolites thereof, present in the original sample. The method of the invention is "label-free," "enzyme-free," and "aptamer-free" in the sense that the method does not include the use of a label, enzyme or aptamer to detect adenosine or its metabolites.

As used herein, a biological sample is intended to mean any biological fluid, or fraction thereof; or an extract of a cell or tissue, or a supernatant or fraction thereof, that contains adenosine, or one or more intracellular metabolites thereof. A sample can be, for example, obtained from an individual or can be derived from such a specimen. For example, a sample can be a supernatant obtained from a minced tissue section obtained by biopsy. Exemplary samples can also include extracts of cultured fibroblasts and cultured amnionic fluid cells. A sample can also be a biological fluid specimen such as urine, blood, plasma, serum, saliva, semen, sputum, cerebral spinal fluid, tears, mucus, and the like. A sample can be further fractionated, if desired, to a fraction containing particular cell types. For example, a blood sample can be fractionated into serum or into fractions containing particular types of blood cells such as red blood cells or white blood cells (leukocytes). If desired, a sample can be a supernatant from a combination of samples from an individual such as a combination of a tissue and fluid sample, and the like. In particular embodiments, the biological sample has been treated with an acid (e.g., perchloric acid or sulfosalicylic acid) to deproteinate the sample.

In reversed phase HPLC, a solute molecule binds to an immobilized hydrophobic molecule in a polar solvent. This partitioning occurs as a result of the solute molecule tending to have hydrophobic patches at its surface, and binding via those patches to the matrix. A mobile phase dissociates the bound molecule at a point at which the hydrophobic interaction between the exposed patches and the immobilized matrix is less favorable than the interaction between the bound molecule and the solvent. The molecule releases from the matrix and elutes. In certain embodiments of this invention, reversed phase HPLC separation of the components of the biological sample is carried out with a DHBA column (Thermo-Fisher Scientific).

In accordance with this invention, elution of the components of the biological sample is carried out isocratically (i.e., the mobile phase composition does not change during the separation process). As is conventional in the art, the mobile phase of the invention is composed of an aqueous component (e.g., water or buffer) and a solvent. Desirably, the solvent is an organic solvent such as methanol, tetrahydrofuran or acetonitrile and is present at a level of between 2 and 20%, or more preferably in the range of 2 to 10% (v/v). In certain embodiments, the mobile phase of the invention contains sodium perchlorate and acetonitrile. The pH of the mobile phase can have an important role on the retention of an analyte and can change the selectivity of certain analytes. Therefore, in certain embodiments of this invention, the pH of the mobile phase is acidic, e.g., in the range of 2-5 or 2-4. In particular embodiments, the pH of the mobile phase is in the range of 2 to 3, which was found to provide the best separation and resolution of peak amplitudes. In other embodiments, separation and elution are carried out at room temperature.

Once the components of the biological sample elute from the reversed phase column, fractions are collected. Collection can be manual or automated and is typically carried out at room temperature. Once collected, the fractions are analyzed by an electrochemical detector. Electrochemical detectors respond to substances that are either oxidizable or reducible and the electrical output results from an electron flow caused by the chemical reaction that takes place at the surface of the electrodes. The detector normally has three electrodes, the working electrode (where the oxidation or reduction takes place), the auxiliary electrode and the reference electrode (which compensates for any change in the electrical conductivity of the mobile phase). There are two modes of operation coulometric detection and ampiometric detection. If the reaction at the electrode surface exhausts all the reactant and the current becomes zero, the total charge that passes will be proportional to the mass of solute detected. In this respect, this process is called coulometric detection. If the mobile phase is flowing past the electrodes, the solute will be continuously replaced as the peak passes through the detector. While there is solute present between the electrodes, a current will be maintained (albeit varying in magnitude). The process is called ampiometric detection. In particular embodiments of this invention, the fractions are subjected to coulometric detection.

While the electrochemical detector read-out can directly be used to determine the presence, absence or relative level of adenosine, or a metabolite thereof, in a biological sample, in some embodiments, the levels detected with the electrochemical detector are compared with a standard curve to quantitate the amount of total adenosine, and intracellular metabolites thereof, present in the original sample. The standard curve can be generated prior to or after the biological sample is separated and can be composed of one component, e.g., adenosine, or a combination of components, e.g., ADO, ATP, ADP and/or AMP. Alternatively, an internal standard can be added to the biological sample (e.g., 3,4-dihydroxybenzylamine).

Using the method of this invention, the levels of adenosine, and intracellular metabolites thereof, are simultaneously detected. In particular, the levels of one or more of adenosine, AMP, ADP or ATP. In accordance with this invention, it is possible to achieve sensitivities in the range of 1-1000 µmol/liter of adenosine, AMP, ADP and/or ATP. Given this level of detection, the claimed method finds application in the diagnosis of diseases or conditions resulting from, or associated with, alterations in the levels of adenosine. Such diseases or conditions include, but are not limited to, Parkinson's disease, Schizophrenia, Epilepsy, Stroke, Panic Disorder and other Psychiatric diseases as well as immunological syndromes.

The invention will be further described in the following examples, which do not limit the scope of the invention described in the claims.

EXAMPLE 1

Neurochemical Analysis of Adenosine in Brain

A high throughput neurochemical assay has now been developed for the detection and quantification of adenosine (a brain neurotransmitter and modulator involved in various neurological diseases) by high performance liquid chromatography and an electrochemical detector (HPLC-ECD).

Chemicals. Optima LC/MS grade Acetonitrile, Methanol, Perchloric acid and Phosphoric acid were purchased from ThermoFisher Chemicals (NJ). Adenosine (ADO), adenosine 5'-monphosphate (ADP), adenosine 5'-monophosphate (AMP), sodium dihydrogen phosphate, potassium phosphate, sodium acetate and sodium perchlorate were purchased from Sigma-Aldrich Chemical Co. (St. Louis, Mo.). Adenosine triphosphate disodium (ATP) was purchased from LKT laboratories, St. Paul, Minn.).

Animals. Male C57BL/6J, FVB/NJ, 129P/J and BALB/c were purchased from the Jackson Labs (Bar Harbor, ME), while Swiss Webster (SW) mice were purchased from Harlan (Indianapolis, Ind.). These mice were housed five per cage in the AALAC-certified vivarium at St Jude Children's Research Hospital and were maintained on a 12 hour light-dark cycle (6:00 AM-6:00 PM) in a temperature- and humidity-controlled room with food and water ad libitum. All of the mice in this study were 6-12 months old and weighed between 23-29 grams at the time of sacrifice.

Preparation of Tissue for HPLC-ECD Analysis of Adenosine. Mice were deeply anesthesized with AVERTIN (tribromoethanol) until all deep tendon and corneal reflexes were absent. Mice were subsequently transcardially perfused with ice-cold saline to remove circulating blood, after which brains were rapidly dissected from the calvaria. Brains were then placed in a cooled brain matrix (Model BS-AL-5000C, Braintree Scientific, Braintree, Mass.) and sliced into 2 mm thick sections. Six brain regions were subsequently subdissected using the following coordinates, olfactory bulb, cerebral cortex (Bregma: −1.00-−3.00 mm), striatum (Bregma: +0.00-+2.00 mm), hippocampus (Bregma: 1.00-−3.00 mm), substantia nigra (Bregma: −2.00-−4.00) and brainstem (Bregma: −5.00-−7.00). The whole process took approximately 7 minutes/mouse.

Once the tissues were dissected, the samples were immediately frozen on dry ice, placed into pre-weighed 1.5 ml tubes and stored at −80° C. On the day of analysis, tissue was weighed, thawed and minced in 200 microliters of mobile phase (see below). Tissue samples were homogenized by a hand-held homogenizer (Pellet Pestle Motor, ThermoFisher Scientific) and centrifuged at 13,700 rpm for 27 minutes at 4° C. The resultant pellet and supernate were separated, frozen and stored at −80° C. for no more than two weeks prior to chromatographic analysis.

Preparation of Standard Solutions and Biological Samples. Separate stock solutions of ADO, ATP, ADP and AMP were prepared in Pani mobile phase at 1 mg/ml and stored at 4° C. The working standard solutions were prepared daily by diluting the stock solutions to 1.25, 2.5, 5.0 and 10.0 µg/ml solutions. Ten µl of each stand solution was injected using an autosampler to generate a simulatenous standard curve immediately prior to HPLC-ECD analysis of the brain samples.

The brain samples were prepared using diluents composed of Pani mobile phase (75%) with 0.3N perchloric acid (25%), which gave a recovery of approximately 90% compared to standards.

Comparison of ADO Separation and Quantification Using Different Stationary and Mobile Phases. Two of the key determinants of separation and quantification of purines in HPLC-ECD is the use of the stationary phase (chromatographic column) in combination with the proper electrolyte (mobile phase). Selection of the proper mobile phase is important since one has to properly dissolve the compounds to be measured, while the proper column function to differentially retain solutes based upon hydrophobic interactions with its stationary phase.

Two protocols describing HPLC-ECD identification of adenosine have been described (Henderson & Griffin (1984) J. Chromatograph. 298:231-242; Birbeck, et al. (2012) Pittcon 2012. Orlando. pp. 70). However, these references did not describe the direct and simultaneous detection of adenosine as well as its metabolites, ATP, ADP and AMP. In contrast, the instant HPLC-ECD protocol was developed for simultaneous detection of ADO, ATP, ADP and AMP. Four different columns and five different mobile phases were empirically tested. Each column and mobile phase was used in combination such that 20 possible pairs were tested.

The columns included: (1) ESA, HR80, 4.6×80 mm, C18, 3 micron particle size; (2) ESA, MD-150, 3.2×150 mm, C18, 3 micron particle size; (3) Kinetex 2.1×50 mm, C18, 2.6 micron particle size; and (4) ESA, DHBA-3.2×250 mm, C18, 5 micron particle size.

The mobile phases tested were: (1) sodium phosphate monobasic & dibasic, 1-octanesulphonic acid, acetonitrile and methanol, pH 3.85; (2) sodium phosphate monobasic, 1-octanesulphonic acid; acetonitrile, pH 3.85, (3) potassium phosphate, 1-octanesulphonic acid, EDTA, acetonitrile and methanol, pH 3.5; (4) sodium phosphate, potassium phosphate, 1-octanesulphonic acid, EDTA, methanol and acetonitrile, pH 3.5; (5) a mobile phase (Pani mobile phase) composed of 19.0 mM sodium perchlorate (Fischer Scientific) and 4.0% (v/v) acetonitrile (Optima, LC/MS grade) prepared in double distilled, deionizer, autoclaved water tested at 4 different pH values (1.75, 2.75, 3.75 and 7.0), each adjusted to the target pH with phosphoric acid (85%, Fisher). Buffer (5) was filtered prior to use through a 0.22 µM filter membrane under vacuum and degassed through an ESA model DG4 degasser, and pumped at a rate of 0.5 ml/min, producing a background pressure of approximately 161 BARs.

Empirical data demonstrated good separation of ATP, ADP, AMP and ADO upon elution only with the ESA, DHBA-3.2×250 mm, C18, 5 micron particle size column in combination with the newly formulated mobile phase (Pani mobile phase (5), pH 2.75).

Quantitative Analysis of Adenosine, AMP, ADP and AMP. Adenosine, AMP, ADP and AMP were analyzed using high performance liquid chromatography with electrochemical detection. Briefly, the chromatographic system included a solvent delivery system (ThermoFisher Scientific, model 584 pump) and an autosampler (ThermoFisher Scientific, model 542) equipped with an injection valve containing a 15 µl sample loop. ADO, ATP, ADP and AMP detection was accomplished by means of a coulometric electrochemical detector (Coulochem III, ThermoFisher Scientific). The analytical cell (Boron Doped Diamond (BDD), Electron North America, LLC, Model 5040) was used versus a hydrogen/palladium reference electrode and was set to +1300 mV. This voltage was determined by empirical measurement of all four compounds and then balancing the ratio of oxidative potential to noise at each voltage. Chromatographic separations were performed on a DHBA column (diameter 250×3.2 mm, Thermo-Fisher Scientific) in-line with a pre-column column (Thermo-Fisher), and the entire system was run at ambient temperature.

The signal from the electrochemical detector was recorded using a model SS420x integration device (Scientific Software Inc.) and the retention time of ADO, ATP, ADP and AMP standards (Sigma) were empirically determined. After identification of retention time for each compound, concentration curves, ranging from 0 to 100 ng, were generated and linearity of detection of the analytes was confirmed. Identification of ADO, ATP, ADP and AMP were further confirmed by spiking random samples with external standards and finding no peak shift. ADO, ATP, ADP and AMP concentrations in tissues were quantified by comparing the peak areas of the sample chromatograms with external standard chromatograms. Additionally, re-extraction of the pellets generated during the initial extraction was performed to determine if ADO, ATP, ADP and AMP had been fully extracted. HPLC-ECD analysis of the re-extracted supernatant found no ADO, ATP, ADP or AMP, and on this basis, it was concluded that the peaks co-eluting from mice brain samples, in comparison to the external standard chromatogram, represented a true picture of the levels of ADO and its metabolites in the mouse brain.

EXAMPLE 2

Determination of ADO, ATP, ADP and AMP

To determine the retention time of ADO, ATP, ADP and AMP, purified compounds, i.e., adenosine (99% pure, Sigma, St. Louis, Mo.), adenosine triphosphate disodium (ATP, LKT Laboratories, St. Paul, Minn.), adenosine 5'-diphosphate (ADP, Sigma), and adenosine 5'-monophosphate, (AMP, Sigma) were dissolved in the Pani mobile phase at four different pH values (1.75, 2.75, 3.75 and 7.0). Ten microliters of combined standards and/or samples at each pH were injected into the HPLC at +1300 mV with a flow rate of 0.5 ml/min. It was observed that the best separation and resolution of the peak amplitude occurred at 2.75. Thus, the Pani mobile phase at pH 2.75 was used for all subsequent analyses. The retention time of ADO, ATP, ADP and AMP were subsequently empirically determined. To demonstrate that each of these could be simultaneously detected on a single chromatogram, ten microliters of a 10 mg/ml solution of an equal mixture of ADO, ATP, ADP, and AMP was analyzed. Four distinct peaks showing the individual compounds were resolved and there was no significant difference in the HPLC retention times when compared to their individual elutions.

EXAMPLE 3

Quantification of ADO, ATP, ADP and AMP in Brain

The levels of ADO, ATP, ADP and AMP (pg/mg wet weight of tissue) in six different brain regions of C57BL/6J mice and their contribution to the total purine are listed in Table 1.

TABLE 1

| Brain Region | Adenosine | ATP | ADP | AMP | Total Pool |
|---|---|---|---|---|---|
| Olfactory Bulb | 3041 ± 473 (1%) | 29865 ± 1941 (5%) | 16684 ± 2058 (3%) | 618096 ± 48753 (96%) | 667686 |
| Cerebral Cortex | 12620 ± 2065 (7%) | 89799 ± 14699 (52%) | 12620 ± 4462 (7%) | 56682 ± 4274 (34%) | 171721 |
| Striatum | 184669 ± 25677 (7%) | 682872 ± 65889 (24%) | 289646 ± 15151 (11%) | 1582489 ± 75113 (58%) | 2739676 |
| Hippocampus | 150597 ± 29364 (5%) | 1673536 ± 194710 (52%) | 469903 ± 38866 (15%) | 938762 ± 1392562 (29%) | 3232798 |
| Substantia Nigra | 16029 ± 2265 (3%) | 92867 ± 4860 (19%) | 60929 ± 3930 (13%) | 308429 ± 23553 (65%) | 478254 |
| Cerebellum | 9111 ± 1877 (9%) | 35650 ± 5205 (36%) | 27518 ± 1816 (28%) | 26887 ± 3009 (27%) | 99166 |

Of the six regions examined, the striatum and hippocampus had the highest amounts of total ADO, with cerebral cortex and substantia nigra having intermediate levels, while the olfactory bulb and cerebellum had the lowest levels measured. A similar pattern was observed for ATP, ADP and AMP pools.

EXAMPLE 4

Quantification of ADO in the CNS of Different Mouse Strains

The levels of ADO (pg/mg wet weight of tissue) in 7 different brain regions of five different strains of mice were determined. The statistical significance of the changes among the strains and regions was assessed by ANOVA followed by Bonferroni post hoc analysis using SIGMASTAT software.

In general, the levels of ADO in the brain of each of the strains examined at basal conditions were low, with the exception of the BALB/c strain that had relatively higher ADO levels. In addition to differing levels of ADO among strains, there was also variation in the region examined. Regionally, the highest levels of ADO were seen in the striatum and olfactory bulb and lowest levels were in the brainstem. Significant differences were found among mouse strains in each region examined.

In olfactory bulb, significant differences were seen between the 5 strains (F=32.57, p≤0.0001) with ADO in BALB/c significantly increased compared to the other 4 strains examined. The order of ADO from highest to lowest in the olfactory bulb was BALB/c→SW→FVB/NJ→129P/J→C57BL/6J. The increased ADO in BALB/c ranged from 532% higher than that measured in SW to a 17,566% increase compared to C57BL6/J.

In the striatum, significant differences were noted between the 5 mouse strains (F=26.67, p≤0.0001), with the highest levels of ADO in SW and BALB/c and lowest levels in C57BL6/J. The order of ADO from highest to lowest in striatum was BALB/c→SW→FVB/NJ→129P/J→C57BL/6J. The increased ADO in BALB/c ranged from 162% higher than that measured in BALB/c to a 2480% increase compared to C57BL/6J.

In the cerebral cortex, significant differences were noted between the 5 mouse strains (F=9.322, p≤0.0001) with the higher levels of ADO in SW and BALB/c and lower levels in 129P/J, C57BL/6J and FVB/NJ. The order of ADO from highest to lowest in the cerebral cortex was SW→BALB/c→129P/J→C57BL/6J→FVB/NJ. The increased ADO in SW ranged from 255% higher than that measured in 129P/J to a 415% increase compared to FVB/NJ.

In hippocampus, significant differences were noted between the 5 mouse strains (F=16.70, p≤0.0001), with the highest levels of ADO in 129P/J and BALB/c and lowest levels in SW. The order of ADO from highest to lowest in hippocampus was BALB/c→129P/J→C57BL/6J→FVB/NJ→SW. The increased ADO in BALB/c ranged from 567% higher than that measured in 129P/J to 2787% increase compared to SW.

In substantia nigra, significant differences were noted between the 5 mouse strains (F=22.73, p≤0.0001), with the highest levels of ADO in SW and BALB/c and lowest levels in C57BL/6J and 129P/J. The order of ADO from highest to lowest in substantia nigra was BALB/c→SW→FVB/NJ→129P/J→C57BL/6J. The increased ADO in BALB/c ranged from 258% higher than that measured in FVB/NJ to a 701% increase compared to C57BL/6J.

In brainstem, significant differences were seen among the 5 groups (F=39.81, p≤0.0001), with the highest levels of ADO in SW and BALB/c and lowest levels in C57BL/6J. The order of ADO from highest to lowest in brainstem was BALB/c→SW→FVB/NJ→129P/J→C57BL/6J. The increased ADO in BALB/c ranged from 951% higher than that measured in FVB/NJ to an 1139% increase compared to C57BL/6J.

In cerebellum, significant differences were seen among the 5 groups (F=44.20, p≤0.0001), with the highest levels of ADO in BALB/c and lowest levels in C57BL/6J. The order of ADO from highest to lowest in brainstem was BALB/c→SW→C57BL/6J→SW→FVB/NJ. The increased ADO in BALB/c ranged from 281% higher than that measured in 129P/J to a 793% increase compared to FVB/NJ.

What is claimed is:

1. A method for simultaneously detecting adenosine, and its metabolites in a biological sample, comprising
    (i) separating components of a biological sample by reversed phase high pressure liquid chromatography under isocratic elution conditions using a mobile phase containing sodium perchlorate and acetonitrile at a pH in a range of 2 to 4;
    (ii) collecting fractions; and
    (iii) simultaneously detecting levels of adenosine, and metabolites thereof, in each fraction with a coulometric electrochemical detector.

2. The method of claim 1, further comprising
    (iv) comparing the detected levels of adenosine, and metabolites thereof, with a standard curve to quantitate an amount of adenosine, and metabolites thereof, present in the biological sample.

3. The method of claim 1, wherein step (i) is carried out under acidic conditions.

4. The method of claim 1, wherein the metabolites comprise adenosine monophosphate, adenosine diphosphate, and adenosine triphosphate.

5. A method for simultaneously detecting adenosine, and its metabolites, in a biological sample, consisting of:
    (i) separating components of a biological sample by reversed phase high pressure liquid chromatography under isocratic elution conditions using a mobile phase containing sodium perchlorate and acetonitrile at a pH in a range of 2 to 4;
    (ii) collecting fractions;
    (iii) simultaneously detecting levels of adenosine, and metabolites thereof, in each fraction with a coulometric electrochemical detector; and
    (iv) comparing the detected levels of adenosine, and metabolites thereof, with a standard curve to quantitate an amount of adenosine, and metabolites thereof, present in the biological sample.

6. The method of claim 5, wherein step (i) is carried out under acidic conditions.

7. The method of claim 5, wherein the metabolites comprise adenosine monophosphate, adenosine diphosphate, and adenosine triphosphate.

* * * * *